(12) United States Patent
Lim et al.

(10) Patent No.: US 6,489,128 B1
(45) Date of Patent: Dec. 3, 2002

(54) METHODS FOR DETECTING CANCER OF THE CENTRAL NERVOUS SYSTEM

(75) Inventors: Yow-Pin Lim, East Providence, RI (US); Douglas C. Hixson, Barrington, RI (US)

(73) Assignee: Rhode Island Hospital, A Lifespan Partner, Providence, RI (US)

( * ) Notice: Subject to any disclaimer, the term of this patent is extended or adjusted under 35 U.S.C. 154(b) by 0 days.

(21) Appl. No.: 09/491,479

(22) Filed: Jan. 24, 2000

(51) Int. Cl.[7] .................. G01N 33/574; G01N 33/53; C07K 16/00; C12P 21/08
(52) U.S. Cl. .................. 435/7.23; 435/7.1; 530/388.85
(58) Field of Search ................... 435/7.1, 7.23; 530/388.85

(56) References Cited

PUBLICATIONS

Yoshida, et al., Inflammation, 1994, 18(6):589–596.*
Mizon, et al., 1669, J. Immunol. Methods, 190:61–70.*
Etsuo, Y. et al. (1991) "An Active Component of Inter–Alpha Trypsin Inhibitor in Brain Tissues." JPN J Physiol. No. 41, pp. 109.
Businaro, R. et al. (1992) "Inter–Alpha–Trypsin Inhibitor–Related Immunoreactivity in Human Tissues and Body Fluids" Cellular and Molecular Biology, CMB Associates, Noisy–Le–Grand, Fr., vol. 38 No. 4, pp. 463–471.

Lim, Yow–Pin et al. (2000) "Inter–Alpha Trypsin Inhibitor in the Cerebrospinal Fluid of Patients With Primary and Metastatic Brain Cancer Diagnostic and Prognoistic Applications." Proceedings of the American Association for Cancer Research Annual Meeting No. 41, pp. 393.

Chawla, R.K. et al., (1981) "Plasma Inter–α Trypsin Inhibitor (IATI) IN Metastatic Breast Cancer" Oncodev. Biol. Med. vol. 2, No. 5, p. 20 (Abstract 40).

Mizon, C. et al. (1996) "Development of an Enzyme–Linked Immunosorbent Assay For Human Plasma Inter–α–Trypsin Inhibitor (ITI) Using Specific Antibodies Against Each of the $H_1$ and $H_2$ Heavy Chains" Journal of Immunological Methods, vol. 190, pp. 61–70.

Yoshida, Esuo et al. (1994) "Immunohistochemical Demonstration of Bikunin, A Light Chain of Inter–α–Trypsin Inhibitor, In Human Brain Tumors" Inflammation, vol. 18, No. 6, pp. 589–596.

* cited by examiner

Primary Examiner—Anthony C. Caputa
Assistant Examiner—Natalie Davis
(74) Attorney, Agent, or Firm—Ingrid A. Beattie; Mintz Levin Cohn Ferris Glovsky & Popeo, P.C.

(57) ABSTRACT

A method for diagnosing a tumor in the central nervous system of a mammal is carried out by contacting a bodily fluid from the mammal with a ligand which binds to inter-alpha trypsin inhibitor.

2 Claims, 4 Drawing Sheets

SEQUENCE LISTING

<160> NUMBER OF SEQ ID NOS: 6

<210> SEQ ID NO 1
<211> LENGTH: 8
<212> TYPE: PRT
<213> ORGANISM: Homo sapiens

<400> SEQUENCE: 1

```
Arg Gly Pro Cys Arg Ala Phe Ile
 1               5
```

<210> SEQ ID NO 2
<211> LENGTH: 352
<212> TYPE: PRT
<213> ORGANISM: Homo sapiens
<220> FEATURE:
<221> NAME/KEY: SIGNAL
<222> LOCATION: (1)..(19)

<400> SEQUENCE: 2

```
Met Arg Ser Leu Gly Ala Leu Leu Leu Leu Ser Ala Cys Leu Ala
 1               5                  10                  15

Val Ser Ala Gly Pro Val Pro Thr Pro Pro Asp Asn Ile Gln Val Gln
             20                  25                  30

Glu Asn Phe Asn Ile Ser Arg Ile Tyr Gly Lys Trp Tyr Asn Leu Ala
         35                  40                  45

Ile Gly Ser Thr Cys Pro Trp Leu Lys Lys Ile Met Asp Arg Met Thr
     50                  55                  60

Val Ser Thr Leu Val Leu Gly Glu Gly Ala Thr Glu Ala Glu Ile Ser
 65                  70                  75                  80

Met Thr Ser Thr Arg Trp Arg Lys Gly Val Cys Glu Glu Thr Ser Gly
                 85                  90                  95

Ala Tyr Glu Lys Thr Asp Thr Asp Gly Lys Phe Leu Tyr His Lys Ser
                100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
        130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
        195                 200                 205

Pro Gln Glu Glu Glu Gly Ser Gly Gly Gly Gln Leu Val Thr Glu Val
    210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255
```

-continued

```
Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
                340                 345                 350

<210> SEQ ID NO 3
<211> LENGTH: 14
<212> TYPE: PRT
<213> ORGANISM: Homo sapiens

<400> SEQUENCE: 3

Ala Val Leu Pro Gln Glu Glu Glu Gly Gly Gly Gly Gly Gln
  1               5                   10

<210> SEQ ID NO 4
<211> LENGTH: 14
<212> TYPE: PRT
<213> ORGANISM: Homo sapiens
<220> FEATURE:
<223> OTHER INFORMATION: Xaa at position 6 may be any amino acid.

<400> SEQUENCE: 4

Ser Leu Pro Gly Glu Xaa Glu Glu Met Met Glu Glu Val Asp
  1               5                   10

<210> SEQ ID NO 5
<211> LENGTH: 15
<212> TYPE: PRT
<213> ORGANISM: Homo sapiens

<400> SEQUENCE: 5

Ala Val Leu Pro Gln Glu Glu Glu Gly Gly Gly Gly Gly Gln Leu
  1               5                   10                  15

<210> SEQ ID NO 6
<211> LENGTH: 15
<212> TYPE: PRT
<213> ORGANISM: Homo sapiens
<220> FEATURE:
<223> OTHER INFORMATION: Xaa at position 6 may be any amino acid.

<400> SEQUENCE: 6

Ser Leu Pro Gly Glu Xaa Glu Glu Met Met Glu Glu Val Asp Gln
  1               5                   10                  15
```

METHODS FOR DETECTING CANCER OF THE CENTRAL NERVOUS SYSTEM

BACKGROUND OF THE INVENTION

The invention relates to cancer diagnosis.

Effective treatment for patients with cancers of the central nervous system (CNS) is, for the most part, an unmet challenge, and the incidence of both primary and metastatic brain tumors appears to be increasing. The prognosis of patients with malignant gliomas and brain metastases remains poor.

Cytological examination to detect malignant cells in the cerebrospinal fluid (CSF) is a standard method by which diseases such as leptomeningeal carcinomatosis are diagnosed. The absence of malignant cells is a primary endpoint for most therapeutic interventions. However, false negatives are often encountered. The inability to estimate or detect the residual burden of disseminated cells by conventional imaging technologies (computerized axial tomography (CT) scan or magnetic resonance imaging (MRI)) compromises decision making on prognosis and treatment.

SUMMARY OF THE INVENTION

The invention provides an accurate and reliable method of diagnosing primary brain tumors or brain metastases. A method for diagnosing a tumor in the CNS of a mammal is carried out by contacting a bodily fluid from the mammal with a detectable ITI ligand and measuring the amount of bound ITI ligand in the sample of bodily fluid. For example, the ligand is a monoclonal antibody or polyclonal antisera which binds to an ITI polypeptide, e.g., an ITI light chain polypeptide; a sample of bodily fluid is contacted with the antibody under conditions sufficient to form an antigen-antibody complex and the complex(es) detected. Alternatively, the ligand is a synthetic or proteolytically-generated peptide that binds to the ITI light chain. For detection purposes, the ligand, e.g., ITI-specific antibody, is directly or indirectly labelled using, e.g., a calorimetric or radioisotopic marker. The amount of the immune complex (which contains ITI antigen bound to ITI-specific antibody) is quantitated to determine the level of ITI in the fluid, and the level of ITI in the fluid is compared to a normal control level of ITI (e.g., a previously determined baseline value or the level of ITI from a subject known to be cancer-free). ITI is elevated in the bodily fluids of patients with CNS tumors as a result of secretion of ITI by disseminated cancer cells or as a result of breakdown of the ECM, which causes leakage of serum ITI into the CSF. Alternatively, tumor cells stimulate production of ITI by surrounding tissues in the brain such as choroid plexus and astrocytes. An elevated level of ITI compared to a normal control level indicates the presence of a tumor in the CNS of the tested mammal. For example, the presence of a tumor is indicated by an amount of ITI in a test sample which is at least two-fold greater than that in a normal control or normal baseline amount of ITI in a CNS bodily fluid such as (CSF). For example, the amount of ITI in the test sample is 2–7 fold greater than normal. The level of ITI in a CNS bodily fluid is indicative of a neurological tumor.

The bodily fluid is a preferably a CNS-derived fluid. By CNS is meant a bodily tissue of the brain or spinal cord. For example, a CNS-derived fluid is cerebrospinal fluid or the supernatant of a cell lysate of cells of the brain, spinal cord, or cells found in the CSF. Other bodily fluids such as blood, serum, urine, saliva, sputum, perspiration, lung effusion, or ascites fluid are tested for the level of ITI as an indication of CNS pathology.

Also with the invention is a method for prognosis of a tumor in the CNS of a mammal, which is carried out by (a) contacting a bodily fluid, e.g., a CNS-derived fluid, from the mammal with an antibody reactive with an ITI polypeptide, e.g., an ITI light chain, under conditions sufficient to form an antigen-antibody complex and detecting the antigen-antibody complex; (b) quantitating the amount of complex to determine the level of ITI in the fluid; and (c) comparing the level of ITI in the fluid with a normal control level of ITI. Changes in the severity of the disease are monitored by comparing changes in the level of ITI in bodily fluids of the patient over time. An increasing level of ITI, e.g., in the CSF, over time indicates an adverse prognosis, e.g,. increased CNS pathology. Such temporal data is used to determine a course of treatment for the patient.

The invention features a monoclonal antibody that binds to an epitope of ITI light chain. The antibody binds to residues within or proximal to an active site of the ITI light chain. When incubated in the presence of ITI and a serine protease, the antibody inhibits ITI-mediated inhibition of serine protease activity. Preferably, the antibody, e.g., mAb 69.31, does not bind to an octapeptide sequence of Urinary Trypsin Inhibitor fragment (UTI), Arg-Gly-Pro-Cys-Arg-Ala-Phe-Ile (SEQ ID NO:1).

Reagents, e.g., an ITI-specific antibody such as mAb 69.31, for carrying out the diagnostic or prognostic assay may be packaged together as a kit. For example, the antibody is immobilized on a solid phase and packaged together with other reagents suitable for detecting ITI-ligand complexes. For example, enzyme-conjugated reagents may be included; ITI may also be included as a standard or control reagent. The solid phase component of the kit onto which an antibody or antigen is immobilized is preferably an assay plate, an assay well, a nitrocellulose membrane, a bead, a dipstick, or a component of an elution column. For example, the capture antibody, e.g., mAb 69.31, is immobilized and a secondary antibody is used to detect the immune complex (e.g., an ITI antigen bound to the mAb 69.31 antibody. The kit may optionally contain a purified ITI polypeptide or purified ITI complex as a control. The polypeptide or complex is purified from natural sources or recombinantly produced. The kit may also contain a second antibody or other detectable marker. The second antibody or marker is labelled, e.g., using a radioisotope, fluorochrome, or other means of detection.

Also within the invention is a method of inhibiting metastases of a systemic cancer into the CNS of a mammal by administering to the mammal an ITI composition, e.g., an ITI polypeptide or a nucleic acid encoding an ITI polypeptide. For example, a sythetic oligonucleotide encoding an ITI polypeptide is administered. The ITI composition is administered by infusion directly into the CSF of the mammal. For therapeutic administration, the ITI polypeptide is administered in its native form as a molecular complex in which an ITI light chain is bound to an ITI heavy chain. The method may include a step of identifying a mammal at risk of developing a brain metastases. For example, the following cancers have a tendency to metastasize to the CNS, e.g, the brain: breast cancer, lung cancer, ovarian cancer, kidney cancer, malignant melanoma, esophageal cancer, head and neck cancers, testis cancer, choriocarcinoma, prostate cancer, bone cancers, and soft tissue sarcomas. Individuals diagnosed as having such cancers are among those at risk of developing a metastases of the cancer to the CNS. Individuals suspected of having CNS cancer are also identified by detecting clinical symptoms such as headache, nausea or vomiting, seizures, altered mental status, altered speech, visual abnormalities, and/or paralysis. A CT scan or MRI is often used to diagnose brain metastases. However, the assays of the invention provide significant advantages, e.g., increased sensitivity, over such conventional diagnostic tools. The claimed assays accurately and reliably detect the presence of tumor very early (prior to the time at which a tumor is detected by the appearance of physical symptoms or by CT or MRI).

A method of inhibiting metastases of a primary CNS cancer in a mammal is also within the invention. The therapy is carried out by administering to into a mammal an ITI polypeptide, e.g., by direct infusion into the CSF of the mammal. Individuals having been diagnosed with the following CNS cancer types are treated according to the invention: astrocytoma, glioma, or metastases into the brain from other cancer types such as leukemias or carcinomas.

Other features and advantages of the invention will be apparent from the following detailed description, the drawings, and the claims.

BRIEF DESCRIPTION OF THE DRAWING

As shown in FIGS. 3 and 4, in the absence of ITI, PC-3 cells migrated into MATRIGEL® after 48 hours. With the addition of 10 nM purified ITI, the migration was completely inhibited. Further incubation with increasing amounts of purified mAb 69.31 effectively blocked the inhibitory activity of ITI. Incubation with mAb 69.31 alone had little or no effect on the migration of PC-3 cells. Incubation with an unrelated antibody (mAb 69.20) did not affect the inhibitory activity of ITI. These results indicate that the blocking effect of mAb 69.31 was specific and that mAb 69.31 recognizes an epitope in the light chain of ITI which is important for the protease inhibitory activity of ITI.

DETAILED DESCRIPTION

Figure 1:
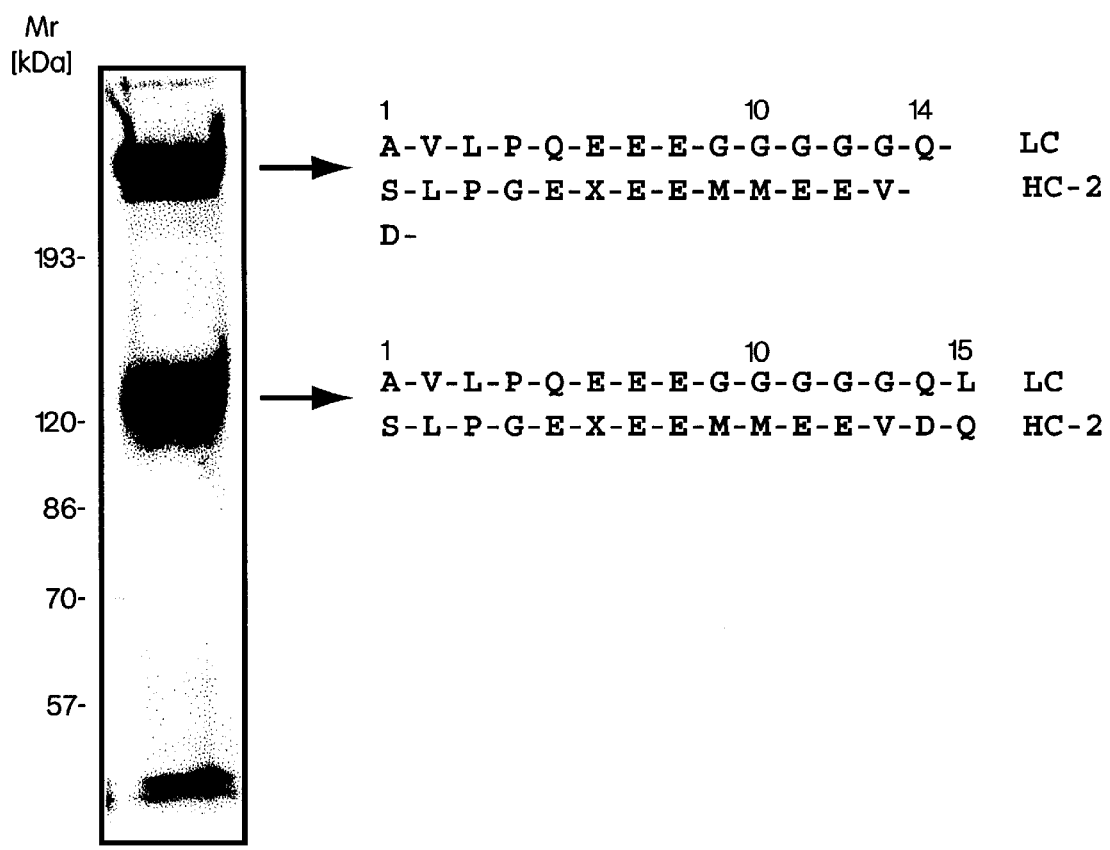
FIG. 1 is a photograph of an electrophoretic gel. Proteins were affinity purified with immobilized mAb 69.31; native molecular complex of ITI light chain complexed with heavy chain was precipitated. Proteins eluted from the affinity column were subjected to SDS-PAGE; the purified proteins were visualized by silver staining. A band at approximately 250 kDa and one at 125 kDa were detected. The bands were identified as ITI heavy chain (HC-2) and light chain (LC) by N-terminal amino acid sequence analysis. The two bands represent an ITI complex which contains a single LC and a single HC (125 kDa) and a single LC with two HC (250 kDa).

Detection of ITI in bodily fluids is a sensitive and reliable method of diagnosing primary brain tumors or metastatic involvement in the CNS of cancer which originated elsewhere in the body. An increase in ITI levels was detected in the bodily fluids, e.g., CSF, of patients with primary and metastatic brain tumors. Tumor cells produce proteases that induce ITI expression in surrounding tissues such as choroid plexus and/or degradation of the extracellular matrix (ECM), resulting in leakage of serum ITI into the CSF.
Production of ITI-specific Antibodies A panel of mabs was generated against two different human plasma-derived Factor VII preparations using a standard subtractive immunization protocol. The mice were first immunized with a non-pasteurized preparation (containing ITI), treated with cyclophosphamide, and then injected with a pasteurized preparation. Following sacrifice of the mice, hybridomas were generated and screened using known methods. One of the antibodies (mAb 69.31) was found to bind to a complex glycoprotein which contains several polypeptide chains. Affinity chromatographic purification of the antigen complex with immobilized mAb 69.31 isolated polypeptide antigens of 250 kDa and 125 kDa in size. The bands (on SDS-PAGE) were identified as ITI by N-terminal amino acid sequence analysis (FIG. 1); AVLPQEEGGGGGO (SEQ ID NO:3); SLPGEXEEM-MEEVD (SEQ ID NO:4); AVLPQEEEGGGGGQL (SEQ ID NO:5); SLPGEXEEMMEEVDQ (SEQ ID NO:6). Affinity-purified ITI inhibited serine proteases, such as trypsin, plasmin, and elastase.

ITI found in the serum or plasma of human subjects contains one light chain and two heavy polypeptide chains covalently linked by a chondroitin sulfate chain. The light chain (with an apparent molecular mass of 30 kDa) inhibits several serine proteases such as trypsin, human leukocyte elastase (HLE), plasmin and cathepsin G, which proteases are involved in inflammation, shock, tumor invasion, and formation of metastases. Naturally-occurring and recombinant ITI light chains are purified with ITI mAb such as 69.31. Purified ITI light chains are useful to therapeutically inhibit serine proteases.

Deposit

A hybridoma cell line RI 69.31 which produces mAb 69.31 has been deposited with the American Type Culture Collection (ATCC) under the terms of the Budapest Treaty on the International Recognition of the Deposit of Microorganisms for the Purpose of Patent Procedure on Dec. 16, 1999, and bears the Patent Deposit Designation PTA-1066. Applicants' assignee acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

Binding Specificity of ITI-specific Antibodies

MAb 69.31 was reactive with the light chain of ITI. ITI was purified from human serum by using mAb 69.31 and treated with 0, 1, 5, and 10 $\mu$g hyaluronidase to cleave the heavy and light chains of ITI. The samples were separated on 12.5% SDS-PAGE and transferred onto nitrocellulose membrane for analysis by Western blot. Without hyaluronidase, two major bands (250 kDa and 125 kDa) were detected with mAb 69.31. With increasing amounts of hyaluronidase, an additional lower molecular weight band (approximately 25–30 kDa) was detected by the antibody. This lower band represented the light chain of ITI. The light and heavy chains of ITI are linked by glycoaminoglycan. Hyaluronidase cleaved the glycoaminoglycan (chondroitin sulfate) chain linking the heavy chain and light chains of the ITI complex, releasing the two chains. These results indicate that mAb 69.31 binds to an epitope located in the light chain of ITI.

Figure 2:
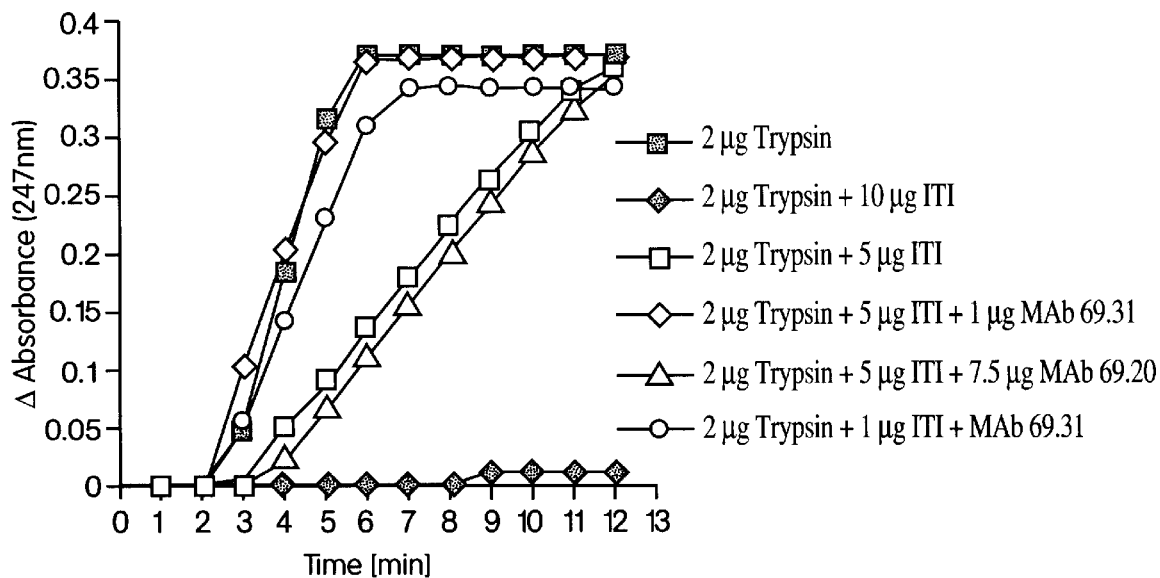
FIG. 2 is a line graph showing the inhibitory activity of ITI. The ability of ITI to inhibit trypsin hydrolysis of P-toluenesulphonyl-L-arginine methyl ester (TAME) was measured electrophoretically. Trypsin alone showed a typical activity curve (□). Affinity purified ITI inhibited trypsin activity in a concentration dependent manner [partial inhibition at 5 μg ITI (■)] and complete inhibition at 10 μg ITI (♦). The addition of purified mAb 69,31 abolished the inhibitory activity of ITI to decrease trypsin hydrolytic activity (●). This effect was specific because addition of other antibodies, e.g., mAb 69.20 (specific for von Willebrand Factor), did not block the inhibitory activity of ITI (Δ), and the addition of mAb 69.31 alone to trypsin did not have any significant effect on trypsin activity (◊).

The addition of mAb 69.31 to ITI blocked the serine protease inhibitory activity of ITI (as demonstrated by the observed reduction in ITI's inhibition of trypsin activity in the presence of the antibody; FIG. 2). These data indicate that the epitope of mAb 69.31 is located in or proximal to the active site of the ITI molecule, i.e., when the 69.31 antibody binds to an ITI light chain molecule, the molecule cannot bind to its substrate. Alternatively, antibody binding alters the 3-dimensional confirmation of ITI, thereby decreasing its serine protease inhibitory acitivity. Other monoclonal antibodies with the binding specificity of mAb 69.31 are produced and identified using methods known in the art, e.g., competitive binding assays. For example, the active site of ITI light chain contains residues 20–32, residues 241–242, or residues 297–298 of SEQ ID NO:2 (Table 2).

ITI Inhibits Metastasis of Tumor Cells

Figure 3:
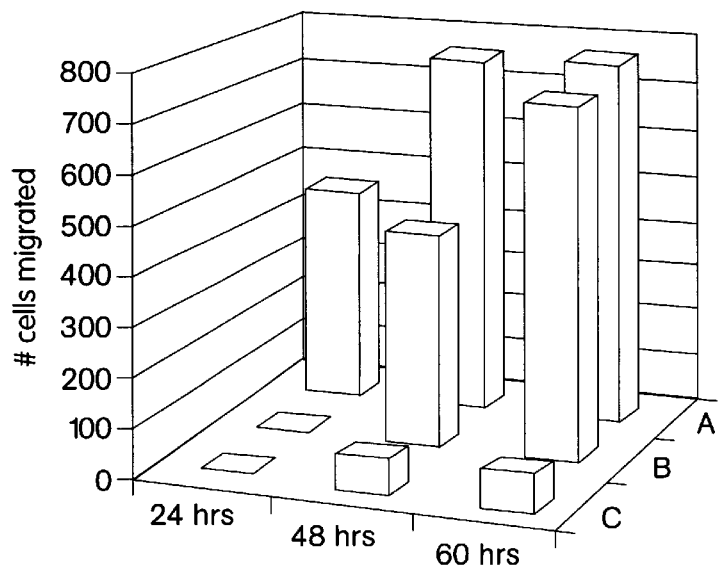
FIG. 3 is a bar graph showing the results of a cell invasion assay. The invasiveness of three different human cell lines were tested in the in vitro three-dimensional cell invasion assay. This assay is based on the ability of invasive cancer cells to migrate through an artificial basement membrane (MATRIGEL®; Becton Dickinson). This migration of the cells is time dependent and also cell type dependent. K-562, a human leukemia cell line (A), was the most invasive of the three cancer cell lines tested. Within 24 hours, cells were already found on the membrane underlying the MATRIGEL® while the human prostate cancer cell line, PC-3 (B), did not reach the membrane before 48 hours. A non-metastatic subpopulation (clone D) of human colon adenocarcinoma cell line DLD-1 (C) was used as a control. Only a few DL-1 cells reached the bottom of the MATRIGEL® after 48 and 60 hours.
Figure 4:
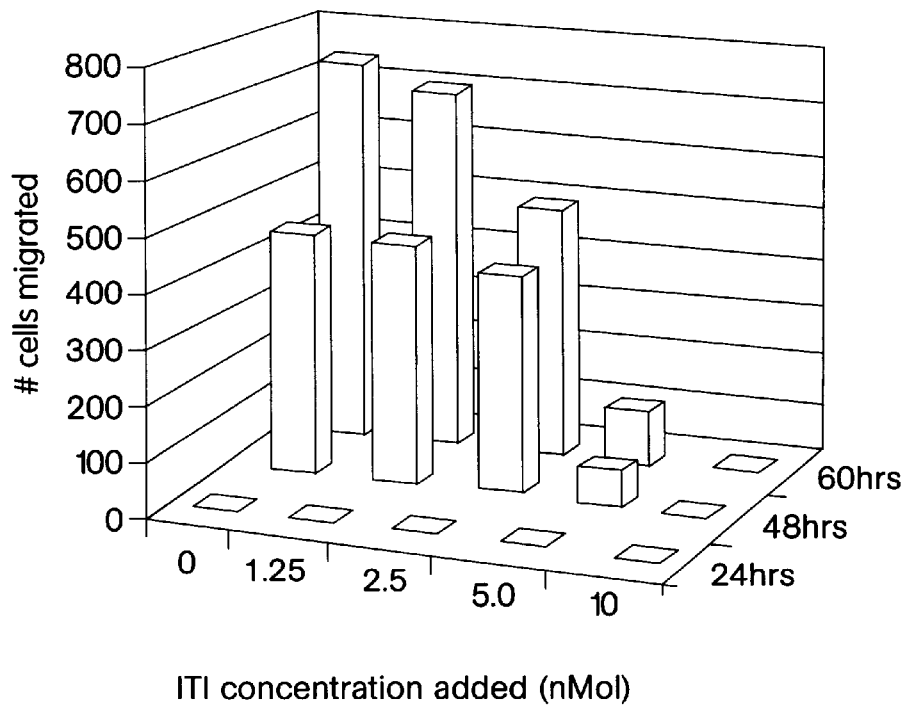
FIG. 4 is a bar graph showing that the incubation of PC-3 cells with the affinity-purified ITI is a very effective method for controlling invasive potential. The addition of ITI greatly hindered migration through MATRIGEL® and cells remained on top of the MATRIGEL® or remained very close to the surface of the membrane. In contrast, without ITI (0 nMol), high levels of migration of cancer cells were detected at 48 and 60 hours. The effect of ITI on cell migration was concentration dependent. With 10 nM ITI, invasion of PC-3 cells was completely inhibited after a 60 min. incubation.
Figure 5:
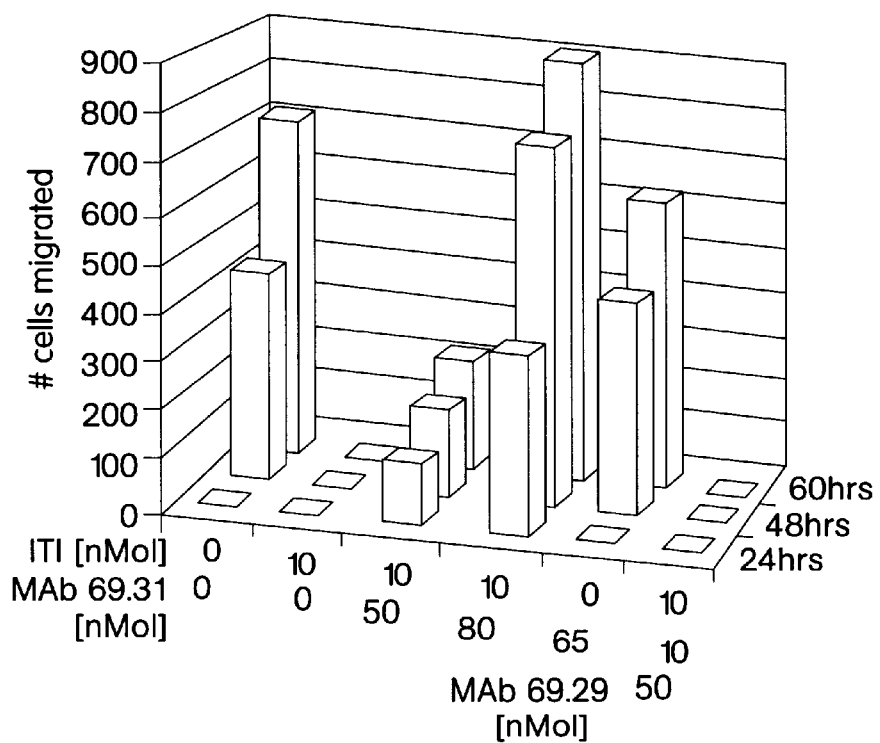
FIG. 5 is a bar graph showing blocking of inhibitory activity of ITI by mAb 69.31 in the PC-3 cell invasion assay.

To evaluate the therapeutic effect of ITI as a anti-metastatic agent, an in vitro three-dimensional cell invasion assay was carried out. The assay is based on the ability of invasive tumor cells to migrate through an artificial basement membrane (MATRIGEL®). Three different cancer cell types with various degrees of invasiveness were tested. Human prostatic cancer cells, PC-3 cells, were less invasive in this assay than human leukemic cells, K562. The non-metastatic human colon adenocarcinoma cell line, Clone D of DLD-1, was used as a negative control (FIG. 3). When ITI was added to PC-3 cells, migration of the cells was inhibited (FIG. 4). The inhibitory activity of ITI was concentration dependent and specifically abolished by the addition of mAb 69.31 (FIG. 5). In contrast, addition of an unrelated antibody (mAb 69.20; negative control antibody which binds to von Willebrand Factor) had little or no effect on the ability of ITI to inhibit metastases.

Clinical Correlation of ITI Levels in Bodily Fluids with CNS Cancers and Metastatic Involvement of CNS Levels of ITI correlate closely with tumor burden and disease progression. Detection of ITI in CSF is also a more accurate predictor of the presence of tumor cells in CSF than conventional CSF cytology.

Figure 6:
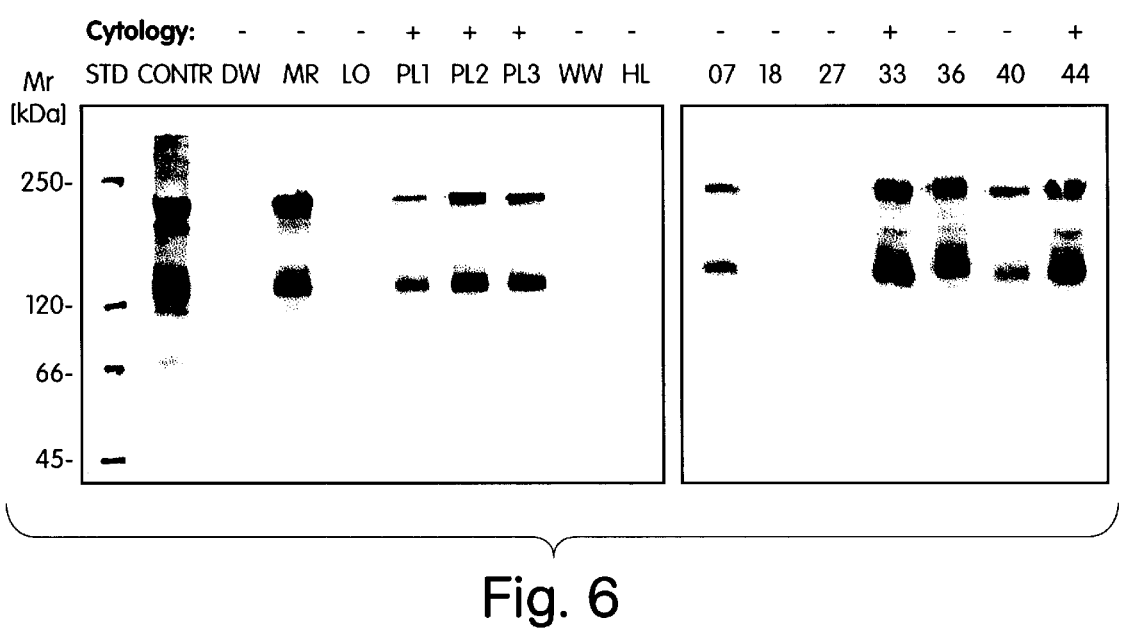
FIG. 6 is an autoradiograph of a Western blot analysis of CSF. 10 μl CSF obtained from a human subject was separated by 6% SDS-PAGE under non-reducing conditions and transferred onto a nitrocellulose membrane for Western blot analysis using mAb 69.31. Two major bands were detected by mAb 69.31 (indicated by the arrows) in CSF that corresponded to those of ITI, which were affinity purified from serum (lane labelled "Contr"). Molecular weight markers were run in the lane labelled "Std". The cytology findings are indicated on top of the patient initials or numbers ("+" indicates detection of malignant cells by standard cytology; "–" indicates no detection of malignant cells by standard cytology.

When CSF of brain cancer patients was analyzed by Western blot using an ITI light chain-specific antibody, significantly higher amounts of ITI were detected compared to CSF from non-tumor control patients (e.g., patients with headache which had previously determined to be cancer-free) or from patients with systemic cancer without demonstrable CNS involvement (FIG. 6). The data shown in FIG. 6 indicate that the ITI diagnostic assay described herein is significantly more sensitive than standard diagnostic tests for neurological tumors, e.g., cytological examination for malignant cells. In some cases, ITI levels in serum of cancer patients may be decreased compared to normal controls, whereas CSF levels are increased compared to normal CSF controls. Elevated CSF levels reliably indicate tumor presence or increased tumor load in the CNS.

For example, when CSF was analyzed by quantitative immunoassay using an ITI light chain-specific monoclonal antibody, e.g., mAb 69.31, in a competitive ELISA, the level of non-tumor control patients or patients with cancer without demonstrable CNS disease was in the range of 0.5–1.0 $\mu$g/ml. Patients with non-tumor neurological disease included those with headache, dementia, and encephalopathies of various etiologies). In contrast, the ITI levels in the CSF of patients with primary or metastatic brain cancer was found to be in the range of 2.0–20 $\mu$g/ml. The levels of ITI correlated closely with tumor burden, disease progression, and response to anti-cancer treatments.

High levels of ITI were detected in CSF of patients (compared to normal control samples or subjects known not to have CNS cancer) with primary brain tumors: MR= [glioblastoma multiforme (GBM)+neoplastic meningitis (NM)]; 07=Medulloblastoma+NM; 33=(GBM+NM); and 40=Astrocytomas) or systemic cancer with CNS involvement (PL=Breast Ca+progressive NM, collected at three different timepoints (PL1–post-radiation therapy; PL2– newly recurrent NM; and PL3–immediately post-radiation therapy (PL3 samples taken after PL2 samples); 36=Lung Ca+NM; and 44=Breast Ca+NM). In contrast, low levels or no ITI was detected in CSF of patients diagnosed as having no tumors: (LO=headache; WW=headache; HL=hydrocephalus; 18=dementia; and 27=encephalopathy) or systemic cancer without CNS involvement (DW=Breast Ca).

Standard methods were used to obtain bodily fluids, e.g., CSF specimens, from various human subjects (individuals with a diagnosis of brain cancer or metastases and individuals with no detectable brain cancer or metastases). CSF specimens were coded, and the ITI analysis was run in a double-blind manner (i.e., without information on patient age, diagnosis, or other clinical characteristics). A total of 49

CSF samples form CNS tumor patients and 20 non-tumor samples were evaluated. The results are summarized in Table 1.

With an overall sensitivity of 86% and a specificity of 95%, the detection of ITI in CSF provides a more reliable, sensitive, and accurate measure of leptomeningeal spread of tumor than conventional CSF cytology (Table 1). Quantitation of ITI levels in CSF correlates with tumor burden in primary and metastatic brain tumors. These results indicate that not only is ITI detection a better diagnostic tool than is currently available, it can be used to distinguish recurrent tumor from treatment effect (e.g., following radiation therapy of a patient), provide early indication of tumor recurrence or malignant change, assess response to therapy, and as a prognostic tool.

TABLE 1

Summary of the detection of ITI and cytological findings of CSF from various patients

|  | Pos. Cytol. | Neg. Cytol. | Pos. ITI Blot | Neg. ITI Blot |
| --- | --- | --- | --- | --- |
| Primary Brain Tumor | 7/24 | 17/24 | 22/24 | 2/24 |
| N = 24 | (29%) | (71%) | (92%) | (8%) |
| Brain Tumor Mets | 11/17 | 6/17 | 13/17 | 4/17 |
| N = 17 | (65%) | (35%) | (76%) | (24%) |
| Neoplastic | 8/8 | 0/8 | 7/8 | 1/8 |
| Meningitis | (100%) | (0%) | (88%) | (12%) |
| N = 8 |  |  |  |  |
| Total CNS Tumor | 26/49 | 23/49 | 42/49 | 6/49 |
| N = 49 | (53%) | (47%) | (86%) | (12%) |
| Systemic Cancer | 0 | 12/12 | 1/12* | 11/12 |
| N = 12 | (0%) | (100%) | (8%) | (92%) |
| Non-tumor control | 0 | 8/8 | 0/8 | 8/8 |
| N = 8 | (0%) | (100%) | (0%) | (100%) |
| Total Non-CNS | 0 | 20/20 | 1/20 | 19/20 |
| N = 20 | (0%) | (100%) | (5%) | (95%) |

*Despite a single negative CSF cytology, this patient had a markedly elevated ITI level, and a neurologic examination that provided compelling evidence for carcinomatous meningitis.

Diagnostic/Prognostic Assays and Kits

The data described herein demonstrated that significantly higher levels of ITI were detected by Western blot in CSF of patients with brain tumors in contrast to the non-tumor control patients or patients with systemic cancer without demonstrable CNS disease. While Western blot assays offer high specificity in detecting ITI, a quantitative assay such as ELISA is preferred to quantify the levels of ITI in bodily fluids is preferred. Not only does the ELISA format facilitate analysis of large numbers of patient specimens to determine the specificity and sensitivity of the ITI as a marker for diagnostic/prognostic purposes, but this type of assay also allows the determination of a normal value range of ITI levels in "non-malignant" CSF. For example, a standard competitive ELISA format using affinity purified human ITI and Mab 69.31 is used to quantify patient ITI levels. Alternatively, a sandwich ELISA using a capture antibody (Mab 69.31) and a second enzyme-labeled rabbit polyclonal antibody against ITI as a detection antibody is used.

Methods of detecting level of ITI in bodily fluids include contacting a component of a bodily fluid with an ITI-specific antibody bound to solid matrix, e.g., microtliter plate, bead, dipstick. For example, the solid matrix is dipped into a patient-derived sample of a bodily fluid, washed, and the solid matrix contacted with a reagent to detect the presence of immune complexes present on the solid matrix.

Proteins in a test sample are immobilized on (bound to) a solid matrix. Methods and means for covalently or noncovalently binding proteins to solid matrices are known in the art. The nature of the solid surface may vary depending upon the assay format. For assays carried out in microtiter wells, the solid surface is the wall of the well or cup. For assays using beads, the solid surface is the surface of the bead. In assays using a dipstick (i.e., a solid body made from a porous or fibrous material such as fabric or paper) the surface is the surface of the material from which the dipstick is made. Examples of useful solid supports include nitrocellulose (e.g., in membrane or microtiter well form), polyvinyl chloride (e.g., in sheets or microtiter wells), polystyrene latex (e.g., in beads or microtiter plates, polyvinylidine fluoride (known as IMMULON™), diazotized paper, nylon membranes, activated beads, and Protein A beads. Microtiter plates may be activated (e.g., chemically treated or coated) to covalently bind proteins. The solid support containing the antibody is typically washed after contacting it with the test sample, and prior to detection of bound immune complexes.

A common feature of all of these assays is that an ITI-specific antibody is contacted with a bodily component suspected of containing ITI under conditions that permit the antigen to bind to the antibody forming an immune complex containing the patient ITI bound to an ITI-specific antibody. Such conditions are typically physiologic temperature, pH, and ionic strength. The incubation of the antibody with the test sample is followed by detection of immune complexes by a detectable label. For example, the label is enzymatic, fluorescent, chemiluminescent, radioactive, or a dye. Assays which amplify the signals from the immune complex are also known in the art, e.g., assays which utilize biotin and avidin.

An ITI-detection reagent, e.g., an antibody, is packaged in the form of a kit. The kit may contain in separate containers an antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay may be included in the kit. The assay may be in the form of a standard sandwich ELISA format known in the art.

For example, an ITI capture antibody, e.g., mAb 69.31, is immobilized on a solid matrix such as a porous strip to form at least one ITI detection site. The measurement or detection region of the porous strip may include a plurality of sites containing an immobilized antibody. A test strip may also contain sites for negative and/or positive controls. Alternatively, control sites are located on a separate strip from the test strip. Optionally, the different detection sites may contain different amounts of immobilized antibody, i.e., a higher amount in the first detection site and lesser amounts in subsequent sites. For example, if 20 nanograms of antibody captures the equivalent of 1 nmol/min/ml of ITI, then the first detection site of an assay device might contain 50 nanograms of the antibody while the subsequent sites contain 10, 20, 30, etc. nanograms of antibody. Upon the addition of test sample, the number of sites displaying a detectable signal provides a quantitative indication of the amount of ITI present in the sample. The detection sites may be configured in any suitably detectable shape and are typically in the shape of a bar spanning the width of a teststrip.

A multi-capture assay configuration is prepared such that if a threshold amount of ITI is not present in the test sample, then substantially all of the ITI will bind to the antibody in the first capture site and thus become immobilized at that site. If a greater than threshold amount of ITI is present in the test sample, the remaining ITI binds to subsequent detection zones of immobilized antibody along the length of the teststrip. The greater the amount of ITI in the test sample, the greater the number of capture sites that will display a detectable signal due to the presence of ITI.

Therapeutic Administration of ITI

An ITI polypeptide is administered to a mammal, e.g., a human patient, for the prevention of brain metastases from systemic cancer, the inhibition of tumor spread along white matter and CSF pathways in primary brain tumors, and the treatment of leptomeningeal metastases. Endogenous ITI in the CSF from brain tumor patients is biologically inactive or (despite being elevated compared to normal control levels) is present at levels insufficient for clinically relevant protective and anti-invasive activity.

ITI inhibits the serine protease, plasmin, which is critical for the degradation of the ECM, thereby inhibiting metastasis in the in vivo. High levels of ITI in cancer patients is indicative of a physiological response aimed at countering tumor-related proteolytic activity. However, the secreted ITI is abnormally altered and biologically inactive. Despite the increased α-1-proteinase level, the serum antitryptic capacity of the tumor patient group averaged only 50% of the normal group, indicating that a significant fraction of the secreted proteins in the tumor group was biologically inactive. Furthermore, increased levels of ITI found in the CSF is quantitatively very low compared to the ITI levels found normally in the serum, suggesting that the amount secreted in CSF is not be sufficient for protection. Thus, ITI is administered as a treatment augments endogenous ITI with biologically active (i.e., anti-metastatic) ITI compositions to inhibit metastasis.

An ITI polypeptide or DNA encoding an ITI polypeptide is administered to increase the level of ITI polypeptide in the CSF of cancer patients and thus inhibit tumor cell metastases. ITI polypeptides are administered to the patient into the CSF in a pharmaceutically acceptable carrier such as physiological saline using standard methods. It is expected that an infusion dosage of approximately 1 to 100 μmoles of the polypeptide of the invention would be administered per kg of body weight per day. For example, an ITI complex (light chain in a complex with heavy chain) is administered in standard pharmacological buffer systems, e.g., for CSF, a standard glycine buffer system is used. For pigs and rats, 30 mg/kg of ITI complex is administered. Doses for human patients is extrapolated from animal models using methods known in the art.

A therapeutic ITI polypeptide has an amino acid sequence that is at least 50% identical to a naturally-occurring ITI amino acid sequence, e.g., SEQ ID NO:2. More preferably, the sequence is at least 75% identical, more preferably 85% identical, more preferably 95% identical, more preferably 99% identical, and most preferably 100% identical to a naturally-occurring ITI sequence.

Nucleotide and amino acid comparisons are carried out using the Lasergene software package (DNASTAR, Inc., Madison, Wis.). The MegAlign module used was the Clustal V method (Higgins et al., 1989, CABIOS 5(2):151–153). The parameter used were gap penalty 10, gap length penalty 10.

ITI fragments to be administered are at least 50% (more preferably 99%, and most preferably 100%) identical to a naturally occurring ITI sequence and have a biological activity of a naturally-occurring ITI polypeptide. For example, a biological activity of ITI is reduction of serine protease activity or inhibition of metastasis or invasiveness of cancer cells, e.g., as measured in the 3-D cell invasion assay described herein. The therapeutic polypeptide preferably contains residues 20–32, residues 241–242, or residues 297–298 of SEQ ID NO:2 (Table 2). The polypeptide preferably contains residue 215 which participates in binding to ITI heavy chain via chondroitin sulfate.

TABLE 2

Amino acid sequence of human ITI light chain

MRSLGALLLL LSACLAVSAG PVPTPPDNIQ VQENFNISRI YGKWYNLAIG STCPWLKKIM 61

DRMTVSTLVL GEGATEAEIS MTSTRWRKGV CEETSGAYEK TDTDGKFLYH KSKWNITMES 121

YVVHTNYDEY AIFLTKKFSR HHGPTITAKL YGRAPQLRET LLQDFRVVAQ GVGIPEDSIF 181

TMADRGECVP GEQEPEPILI PRVRRAVLPQ EEEGSGGGQL VTEVTKKEDS CQLGYSAGPC 241

MGMTSRYFYN GTSMACETFQ YGGCMGNGNN FVTEKECLQT CRTVAACNLP IVRGPCRAFI 301

QLWAFDAVKG KCVLFPYGGC QGNGNKFYSE KECREYCGVP GDGDEELLRF SN (SEQ ID NO:2; residues 1–19 = signal peptide)

An ITI polypeptide for therapeutic administration is substantially pure. Preferably, the ITI polypeptide is the mature form of the polypeptide, i.e., it lacks the signal peptide. Polypeptides are "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, e.g., by column chromatography, polyacrylamide gel electrophoresis, or HPLC analysis.

To render the therapeutic peptides less susceptible to cleavage by peptidases, the peptide bonds of a peptide may be replaced with an alternative type of covalent bond (a "peptide mimetic"). Where proteolytic degradation of the peptides following injection into the subject is a problem, replacement of a particularly sensitive peptide bond with a noncleavable peptide mimetic will make the resulting peptide more stable and thus, more useful as a therapeutic. Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

DNA encoding ITI polypeptides is introduced into target cells of the patient by standard vectors and/or gene delivery systems. Suitable gene delivery systems include liposomes, receptor-mediated delivery systems, naked DNA, and viral vectors such as herpes viruses, retroviruses, and adenoviruses, among others.

Other embodiments are within the following claims.

What is claimed is:

1. A method for diagnosing a tumor in the central nervous system (CNS) of a mammal, comprising contacting a CNS-derived bodily fluid from said mammal with a ligand which binds to an inter-alpha trypsin inhibitor (ITI) light chain under conditions sufficient to form an ITI-ligand complex and detecting the complex, wherein said ligand is monoclonal antibody is 69.31 (ATCC Patent Deposit Designation PTA-1066).

2. The method of claim 1, wherein said fluid is cerebrospinal fluid.

* * * * *